United States Patent
Liu

(10) Patent No.: US 9,757,323 B2
(45) Date of Patent: Sep. 12, 2017

(54) VARIABLE COLOR TRANSPARENT LIP BALM AND PREPARATION METHOD THEREOF

(71) Applicant: Guangzhou Sheencolor Cosmetics Co., Ltd.

(72) Inventor: Shisheng Liu, Guangzhou (CN)

(73) Assignee: GUANGZHOU SHEENCOLOR COSMETICS CO., LTD., Guangzhou (CN)

( * ) Notice: Subject to any disclaimer, the term of this patent is extended or adjusted under 35 U.S.C. 154(b) by 0 days.

(21) Appl. No.: 14/798,394

(22) Filed: Jul. 13, 2015

(65) Prior Publication Data

US 2016/0143837 A1   May 26, 2016

(30) Foreign Application Priority Data

Nov. 20, 2014  (CN) .......................... 2014 1 06746453

(51) Int. Cl.
| | |
|---|---|
| *A61K 8/88* | (2006.01) |
| *A61K 8/31* | (2006.01) |
| *A61K 8/37* | (2006.01) |
| *A61K 8/42* | (2006.01) |
| *A61K 8/73* | (2006.01) |
| *A61Q 1/04* | (2006.01) |
| *A61K 8/368* | (2006.01) |
| *A61K 8/63* | (2006.01) |
| *A61K 8/81* | (2006.01) |
| *A61Q 19/00* | (2006.01) |

(52) U.S. Cl.
CPC ................. *A61K 8/88* (2013.01); *A61K 8/31* (2013.01); *A61K 8/368* (2013.01); *A61K 8/37* (2013.01); *A61K 8/42* (2013.01); *A61K 8/63* (2013.01); *A61K 8/73* (2013.01); *A61K 8/8129* (2013.01); *A61Q 1/04* (2013.01); *A61Q 19/001* (2013.01)

(58) Field of Classification Search
None
See application file for complete search history.

(56) References Cited

U.S. PATENT DOCUMENTS

2007/0166255 A1* 7/2007 Gupta ...................... A61K 8/31
424/70.1
2010/0202991 A1    8/2010 Simon et al.

FOREIGN PATENT DOCUMENTS

WO    2009138978 A2    11/2009

* cited by examiner

*Primary Examiner* — Ileana Popa
*Assistant Examiner* — Nicole Babson
(74) *Attorney, Agent, or Firm* — Boag Law, PLLC

(57) ABSTRACT

The present invention provides a variable color transparent lip balm, consisting of following components by weight percent: 4.0 to 5.0% by weight of dibutyl lauroyl glutamide, 2.0 to 3.0% by weight of polyamide-3, 15.0 to 20.0% by weight of bis-stearyl ethylenediamine/neopentyl glycol/stearyl hydrogenated dimer dilinoleate copolymer, 46.65 to 49.60% by weight of C12-15 alkyl benzoate, 1.0 to 3.0% by weight of heptyl undecylenate, 9.0 to 11.0% by weight of C10-30 cholesterol/lanosterol esters, 10.0 to 15.0% by weight of hydrogenated C6-20 polyolefin, 1.5 to 2.5% by weight of dextrin isostearate, 0.05 to 0.1% by weight of eosin yellowish and 0 to 0.8% by weight of excipient. The transparent lip balm of the present invention has good transparency, and excellent variable color effect.

7 Claims, No Drawings

VARIABLE COLOR TRANSPARENT LIP BALM AND PREPARATION METHOD THEREOF

TECHNICAL FIELD

The present invention relates to the field of cosmetic, and particularly a transparent lip balm with color changing function.

BACKGROUND OF THE INVENTION

Lip balm is commonly used as a lip care product, and its appearance and function have been constantly developed and changed. As the appearance of the transparent lip balm, products with more diversified functions are going to become people's daily requirements. However, lip balms in the current market cannot satisfy higher and higher fashion and aesthetic requirements of people.

SUMMARY OF THE INVENTION

It is an object of the present invention to provide a kind of variable color transparent lip balm with good transparency and excellent variable color effect, with regarding to above technical problems to be solved.

It is a further object of the present invention to provide a preparation method of the transparent lip balm described above.

In order to achieve above objects, the present invention provides a variable color transparent lip balm, wherein it consists of following components by weight percent:
 4.0% to 5.0% by weight of dibutyl lauroyl glutamide,
 2.0% to 3.0% by weight of polyamide-3,
 15.0% to 20.0% by weight of bis-stearyl ethylenediamine/neopentyl glycol/stearyl hydrogenated dimer dilinoleate copolymer,
 46.65% to 49.60% by weight of C12-15 alkyl benzoate,
 1.0% to 3.0% by weight of heptyl undecylenate,
 9.0% to 11.0% by weight of C10-30 cholesterol/lanosterol esters,
 10.0% to 15.0% by weight of hydrogenated C6-20 polyolefin,
 1.5% to 2.5% by weight of dextrin isostearate,
 0.05% to 0.1% by weight of eosin yellowish,
 0 to 0.8% by weight of excipient,
 and the sum of weight percent of all above components is 100%.

Preferably, the weight percent of the excipient is 0.8%.

Preferably, the variable color transparent lip balm according to the present invention consists of following components by weight percent:
 4.5% to 5.0% by weight of dibutyl lauroyl glutamide,
 2.5% to 3.0% by weight of polyamide-3,
 17.5% to 20.0% by weight of bis-stearyl ethylenediamine/neopentyl glycol/stearyl hydrogenated dimer dilinoleate copolymer,
 48.13% to 49.60% by weight of C12-15 alkyl benzoate,
 1.0% to 2.0% by weight of heptyl undecylenate,
 9.0% to 10.0% by weight of C10-30 cholesterol/lanosterol esters,
 10.0% to 12.5% by weight of hydrogenated C6-20 polyolefin,
 1.5% to 2.0% by weight of dextrin isostearate,
 0.07% to 0.1% by weight of eosin yellowish, and
 0.8% by weight of excipient;
 the sum of weight percent of all above components is 100%.

Preferably, the variable color transparent lip balm consists of following components by weight percent:
 5.0% by weight of dibutyl lauroyl glutamide,
 3.0% by weight of polyamide-3,
 20.0% by weight of bis-stearyl ethylenediamine/neopentyl glycol/stearyl hydrogenated dimer dilinoleate copolymer,
 49.60% by weight of C12-15 alkyl benzoate,
 1.0% by weight of heptyl undecylenate,
 9.0% by weight of C10-30 cholesterol/lanosterol esters,
 10.0% by weight of hydrogenated C6-20 polyolefin,
 1.5% by weight of dextrin isostearate,
 0.1% by weight of eosin yellowish, and
 0.8% by weight of excipient.

Preferably, the excipient may be, including but not limited to, other components commonly used for cosmetics such as anti-oxidant, activator, preservative, aromatic or mixture thereof, which is allowed to be used on lips according to regulatory requirements. The anti-oxidant includes but is not limited to tocopheryl acetate; the activator includes but is not limited to bisabolol; the preservative includes but is not limited to propyl hydroxybenzoate; and the aromatic includes but is not limited to essence.

The present invention also provides a preparation method of the above variable color transparent lip balm, comprising the steps of:

(1) stirring and mixing dibutyl lauroyl glutamide, polyamide-3, bis-stearyl ethylenediamine/neopentyl glycol/stearyl hydrogenated dimer dilinoleate copolymer, C12-15 alkyl benzoate, heptyl undecylenate, C10-30 cholesterol/lanosterol esters, hydrogenated C6-20 polyolefin and dextrin isostearate thoroughly, then heating them to 130~140° C., until all of them are completely melted and transparent;

(2) adding and stirring eosin yellowish and excipient to mixture of step (1) thoroughly at a temperature of 100° C., whereby a completely dissolved mixture is obtained; and (3) cooling the mixture obtained by step (2) to 95~100° C., then injecting it into a mould, after that, demoulding is performed when it is cooled to 4~12° C.

A transparent product with color changing function is developed in the present invention based on ordinary lip balm. Under normal circumstances, there are not so many raw materials used for making transparent lip balm, wherein only a few of them can be compatible with eosin yellowish. A lip balm with both transparent and variable color effect is achieved through optimizing proper composition formula according to the present invention, and it satisfies consumer's requirements for fashion and aesthetics. The lip balm of the present invention has an orange and transparent appearance. However, when the lip balm is applied on lips, it is orange at first, then it gradually becomes bright red with time, which brings a fantastic feeling for consumers. The variable color lip balm of the present invention makes people experience pleasant feeling brought by lip gloss while enjoying lip care.

DETAILED DESCRIPTION OF THE INVENTION

The invention is further illustrated by the following examples without limiting the scope of the invention to these particular embodiments.

All components are taken according to following weight percents, and all following components are commercially available.

| Group | Component | Example 1 | Example 2 | Example 3 |
|---|---|---|---|---|
| A phase | Dibutyl lauroyl glutamide | 4.00 | 4.50 | 5.00 |
| | Polyamide -3 | 2.00 | 2.50 | 3.00 |
| | Bis-stearyl ethylenediamine/neopentyl glycol/stearyl hydrogenated dimer dilinoleate copolymer(polyamide-8) | 15.00 | 17.50 | 20.00 |
| | C12-15 alkyl benzoate | 46.65 | 48.13 | 49.60 |
| | Heptyl undecylenate | 3.00 | 2.00 | 1.00 |
| | Hydrogenated C6-20 polyolefin | 15.00 | 12.50 | 10.00 |
| | Dextrin isostearate | 2.50 | 2.00 | 1.50 |
| | C10-30 cholesterol/lanosterol esters | 11.00 | 10.00 | 9.00 |
| B phase | Eosin yellowish | 0.05 | 0.07 | 0.10 |
| | Tocopheryl acetate | 0.20 | 0.20 | 0.20 |
| | Bisabolol | 0.50 | 0.50 | 0.50 |
| | Propyl hydroxybenzoate | 0.10 | 0.10 | 0.10 |
| | Total | 100.00 | 100.00 | 100.00 |

Lip balm of each example described above is prepared respectively by steps of:

1. stirring and mixing raw materials of A phase thoroughly, then heating them to 130~140, until they are completely melted and transparent;

2. adding and stirring materials of B phase into A phase thoroughly at a temperature of 100, whereby a completely dissolved mixture is obtained; and 3. cooling the mixture obtained by step 2 to 95~100° C., then injecting it into a mould, after that demoulding is performed when it is cooled to 4~12° C., then a variable color transparent lip balm is obtained.

Testing and using effects of the lip balms obtained in Examples 1~3 are shown in following table:

| Test item | Melting point (Celsius degree) | Breaking strength (g) Diameter of lip balm is 12.7 mm | Variable color effect (Marked according to sensorial performance in actual use) | Transparency |
|---|---|---|---|---|
| Example 1 | 71 | 520 | 4.9 | Good |
| Example 2 | 74 | 570 | 5.0 | Good |
| Example 3 | 76 | 600 | 5.0 | Good |

1. Melting point, tested by the melting point determination method described in appendix VIC of *Chinese Pharmacopeia*, 2010 edition.

2. Breaking strength, tested by lip balm fracture apparatus. Generally, for lip balm with a diameter of 12.7 mm, its breaking strength will be in the range of 400-800 g, so as to ensure it won't be fractured in use.

3. Variable color effect, marked by sensorial and visual assessment in actual use. 5 scores means excellent, 4 scores means good, 3 scores means average, 2 scores means poor, and 1 score means very poor. data from 20 subjects are recorded, and an average value is taken.

4. Transparency, tested by visual assessment.

According to the testing results shown in the above table, it can be seen that the lip balms of Examples 1 to 3 of the present invention behave excellently not only on good transparency but also on variable color effect, and they have suitable hardness and reliable melting point range, producing a high-value application.

What is claimed is:

1. A variable color transparent lip balm, consisting of the following components by weight percent:
   4.0% to 5.0% by weight of dibutyl lauroyl glutamide,
   2.0% to 3.0% by weight of polyamide-3,
   15.0% to 20.0% by weight of bis-stearyl ethylenediamine/neopentyl glycol/stearyl hydrogenated dimer dilinoleate copolymer,
   46.65% to 49.60% by weight of C12-15 alkyl benzoate,
   1.0% to 3.0% by weight of heptyl undecylenate,
   9.0% to 11.0% by weight of C10-30 cholesterol/lanosterol esters,
   10.0% to 15.0% by weight of hydrogenated C6-20 polyolefin,
   1.5% to 2.5% by weight of dextrin isostearate,
   0.05% to 0.1% by weight of eosin yellowish, and
   0 to 0.8% by weight of excipient;
   wherein the sum of weight percent of all above components is 100%.

2. The variable color transparent lip balm of claim 1, wherein the excipient is an anti-oxidant, activator, preservative, aromatic or mixture thereof, which is allowed to be used on lips according to regulatory requirements.

3. The variable color transparent lip balm of claim 1, consisting of the following components by weight percent:
   4.5% to 5.0% by weight of dibutyl lauroyl glutamide,
   2.5% to 3.0% by weight of polyamide-3,
   17.5% to 20.0% by weight of bis-stearyl ethylenediamine/neopentyl glycol/stearyl hydrogenated dimer dilinoleate copolymer,
   48.13% to 49.60% by weight of C12-15 alkyl benzoate,
   1.0% to 2.0% by weight of heptyl undecylenate,
   9.0% to 10.0% by weight of C10-30 cholesterol/lanosterol esters,
   10.0% to 12.5% by weight of hydrogenated C6-20 polyolefin,
   1.5% to 2.0% by weight of dextrin isostearate,
   0.07% to 0.1% by weight of eosin yellowish, and
   0.8% by weight of excipient;
   wherein the sum of weight percent of all above components is 100%.

4. The variable color transparent lip balm of claim 3, wherein the excipient is an anti-oxidant, activator, preservative, aromatic or mixture thereof, which is allowed to be used on lips according to regulatory requirements.

5. The variable color transparent lip balm of claim 1, consisting of the following components by weight percent:
   5.0% by weight of dibutyl lauroyl glutamide,
   3.0% by weight of polyamide-3,
   20.0% by weight of bis-stearyl ethylenediamine/neopentyl glycol/stearyl hydrogenated dimer dilinoleate copolymer,
   49.60% by weight of C12-15 alkyl benzoate,
   1.0% by weight of heptyl undecylenate,
   9.0% by weight of C10-30 cholesterol/lanosterol esters,
   10.0% by weight of hydrogenated C6-20 polyolefin,
   1.5% by weight of dextrin isostearate,
   0.1% by weight of eosin yellowish, and
   0.8% by weight of excipient.

6. The variable color transparent lip balm of claim 5, wherein the excipient is an anti-oxidant, activator, preservative, aromatic or mixture thereof, which is allowed to be used on lips according to regulatory requirements.

7. A method for preparing the variable color transparent lip balm of claim 1, comprising the steps of:
   (1) stirring and mixing dibutyl lauroyl glutamide, polyamide-3, bis-stearyl ethylenediamine/neopentyl glycol/ stearyl hydrogenated dimer dilinoleate copolymer, C12-15 alkyl benzoate, heptyl undecylenate, C10-30 cholesterol/lanosterol esters, hydrogenated C6-20 polyolefinand dextrin isostearate thoroughly, then heating the ingredients to 130-140° C., until all are completely melted and transparent;

(2) stirring and adding eosin yellowish and excipient to the mixture of step (1) thoroughly at a temperature of 100° C., whereby a completely dissolved mixture is obtained; and (3) cooling the mixture obtained by step (2) to 95-100° C., injecting the mixture into a mould and demoulding the mixture when it has cooled to 4-12° C.

\* \* \* \* \*